United States Patent [19]

Lubowitz et al.

[11] Patent Number: 5,151,487
[45] Date of Patent: Sep. 29, 1992

[54] METHOD OF PREPARING A CROSSLINKING OLIGOMER

[75] Inventors: Hyman R. Lubowitz, Rolling Hills Estates, Calif.; Clyde H. Sheppard, Bellevue, Wash.

[73] Assignee: The Boeing Company, Seattle, Wash.

[21] Appl. No.: 798,626

[22] Filed: Nov. 26, 1991

Related U.S. Application Data

[60] Division of Ser. No. 489,205, Mar. 5, 1990, Pat. No. 5,087,701, which is a continuation of Ser. No. 46,202, May 4, 1987, Pat. No. 4,935,523, which is a continuation-in-part of Ser. No. 865,228, May 20, 1986, abandoned, which is a continuation-in-part of Ser. No. 781,487, Sep. 30, 1985, Pat. No. 4,685,620.

[51] Int. Cl.⁵ .................. C08G 73/10; C07D 491/08
[52] U.S. Cl. .................................... 528/170; 526/260; 528/322; 548/431; 548/435; 548/461; 548/465; 548/476; 548/521; 548/549
[58] Field of Search ............... 528/170, 322; 526/260; 548/431, 435, 461, 465, 476, 521, 549

[56] References Cited

U.S. PATENT DOCUMENTS

| | | | |
|---|---|---|---|
| 3,528,950 | 9/1970 | Lubowitz | 260/78.4 |
| 3,920,768 | 11/1975 | Kwiatkowski | 260/837 R |
| 4,051,177 | 9/1977 | Braden et al. | 260/510 |
| 4,075,171 | 2/1978 | D'Alelio | 260/47 CP |
| 4,107,174 | 8/1978 | Baumann et al. | 260/326 NS |
| 4,418,181 | 11/1983 | Monacelli | 525/426 |
| 4,438,280 | 3/1984 | Monacelli | 562/457 |
| 4,476,184 | 10/1984 | Lubowitz et al. | 428/288 |
| 4,604,437 | 8/1986 | Renner | 526/262 |
| 4,739,075 | 4/1988 | Odagiri et al. | 548/431 |
| 4,847,333 | 7/1989 | Lubowitz et al. | 525/432 |
| 4,935,523 | 6/1990 | Lubowitz et al. | 548/431 |
| 5,087,701 | 2/1992 | Lubowitz et al. | 548/431 |

*Primary Examiner*—Morton Foelak
*Attorney, Agent, or Firm*—Senniger, Powers, Leavitt & Roedel

[57] ABSTRACT

Solvent resistance in polyimide, polyamide, and other resins can be improved by capping these resins with mono- or difunctional crosslinking end caps. Imidophenylamines of the general formula:

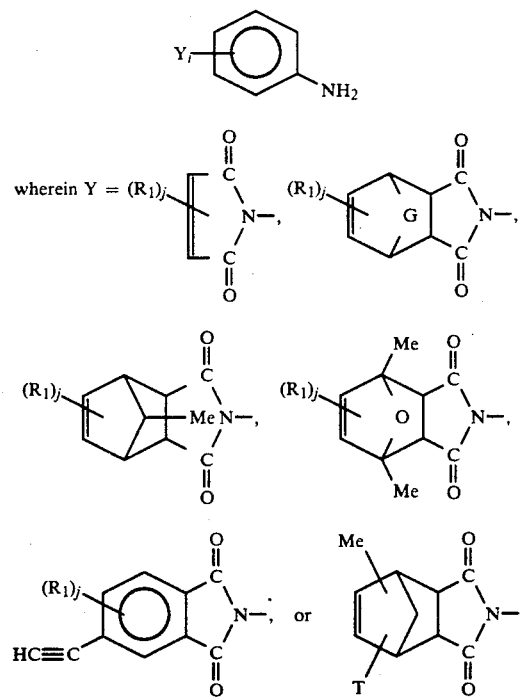

$R_1$ = lower alkyl, lower alkoxy, aryl, aryloxy, substituted alkyl, substituted aryl, halogen, or mixtures thereof;
Me = methyl;
T = allyl or methallyl;
i = 1 or 2;
j = 0, 1 or 2; and
G = —CH$_2$—, —O—, —S—, or —SO$_2$—.

comprise a new family of end cap monomers that are reactants in the synthesis of crosslinking, solvent resistant oligomers.

8 Claims, No Drawings

METHOD OF PREPARING A CROSSLINKING OLIGOMER

REFERENCE TO RELATED APPLICATIONS

This is a divisional application of application Ser. No. 07/489,205, filed Mar. 3, 1990, now U.S. Pat. No. 5,087,701 which was a continuation application of application Ser. No. 07/046,202, filed May 4, 1987, now U.S. Pat. No. 4,935,523, issued Jun. 19, 1990, which was a continuation-in-part application of application Ser. No. 06/865,228, filed May 20, 1986, now abandoned, which was a continuation-in-part application of application Ser. No. 06/781,487, filed Sep. 30, 1985, now U.S. Pat. No. 4,685,620.

TECHNICAL FIELD

The present invention relates to a imidophenylamines of the general formula:

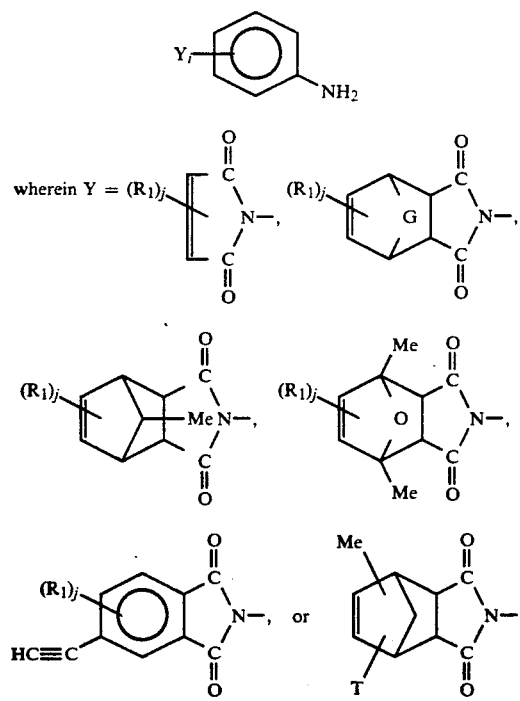

wherein
R$_1$=lower alkyl, lower alkoxy, aryl, aryloxy, substituted aryl, substituted alkyl (either including hydroxyl or halo-substitutents), halogen, or mixtures thereof;
Me=methyl;
T=allyl or methallyl;
i=1 or 2;
j=0, 1, or 2; and
G=—CH$_2$—, —O—, —S—, or —SO$_2$—.

These imidophenylamines are useful in the preparation of solvent resistant advanced composites, such as polyamides or polyimides, when they are condensed into the oligomer to form crosslinking end caps.

BACKGROUND OF THE INVENTION

Recently, chemists have sought to synthesize oligomers for high Performance advanced composites suitable for aerospace applications. These composites should exhibit solvent resistance, toughness, impact resistance, processibility, and strength, and should be thermoplastic. Oligomers and composites that have thermo-oxidative stability, and, accordingly can be used at elevated temperatures are particularly desirable.

While epoxy-based composites are suitable for many applications, their brittle nature and susceptibility to degradation make them inadequate for many aerospace applications, especially those applications which require thermally stable, tough composites. Accordingly, research has recently focused on polyimide composites to achieve an acceptable balance between thermal stability, solvent resistance, and toughness. Still the maximum temperatures for use of the Polyimide composites, such as PMR-15, are about 600°-625° F., since they have glass transition temperatures of about 690° F.

There has been a progression of Polyimide sulfone compounds synthesized to provide unique properties or combinations of properties. For example, Kwiatkowski and Brode synthesized maleic capped linear polyarylimides as disclosed in U.S. Pat. No. 3,839,287. Holub and Evans synthesized maleic or nadic capped imido-substituted Polyester compositions as disclosed in U.S. Pat. No. 3,729,446. We synthesized thermally stable polysulfone oligomers as disclosed in U.S. Pat. No. 4,476,184 or U.S. Pat. No. 4,536,559, and have continued to make advances with polyetherimidesulfones, polybenzoxazolesulfones, polybutadienesulfones, and "star" or "star-burst." multidimensional oligomers. We have shown surprisingly high glass transition temperatures yet reasonable processibility and desirable physical properties in many of these oligomers and their composites.

Polybenzoxazoles, such as those disclosed in our copending applications U.S. Ser. No. 816,490 (to Lubowitz and Sheppard) and 893,124 (to Lubowitz, Sheppard and Stephenson), may be used at temperatures up to about 750°-775° F., since these composites have glass transition temperatures of about 840° F. Some aerospace applications need composites which have even higher use temperatures while maintaining toughness, solvent resistance, processibility, formability, strength, and impact resistance.

Multidimensional oligomers, such as disclosed in our copending applications U.S. Ser. Nos. 726,258; 810,817; and 000,605, have superior processibility over some advanced composite oligomers since they can be handled at lower temperatures. Upon curing, however, the phenylimide end caps crosslink so that the thermal resistance of the resulting composite is markedly increased with only a minor loss of stiffness, matrix stress transfer (impact resistance), toughness, elasticity, and other mechanical Properties. Glass transition temperatures above 950° F. are achievable.

Commercial polyesters, when combined with well-known diluents, such as styrene, do not exhibit satisfactory thermal and oxidative resistance to be useful for aircraft or aerospace applications. Polyarylesters are often unsatisfactory, also, since the resins often are semicrystalline which may makes them insoluble in laminating solvents, intractable in fusion, and subject to shrinking or warping during composite fabrication. Those polyarylesters that are soluble in conventional laminating solvents remain so in composite form, thereby limiting their usefulness in structural composites. The high concentration of ester groups contributes to resin strength and tenacity, but also makes the resin susceptible to the damaging effects of water absorption. High moisture absorption by commercial polyesters can lead to distortion of the composite when it is loaded at elevated temperature.

High performance, aerospace, polyester advanced composites, however, can be prepared using crosslinkable, end capped polyester imide ether sulfone oligomers that have an aeceptable combination of solvent resistance, toughness, impact resistance, strength, processibility, formability, and thermal resistance. By including Schiff base (—CH=N—), imidazole, thiazole, or oxazole linkages in the oligomer chain, the linear, advanced composites formed with Polyester oligomers of our copending application U.S. Ser. No. 726,259 can have semiconductive or conductive properties when appropriately doped.

Conductive and semiconductive Plastics have been extensively studied (see, e.g., U.S. Pat. Nos. 4,375,427; 4,338,222; 3,966,987; 4,344,869; and 4,344,870), but these polymers do not possess the blend of properties which are essential for aerospace applications. That is, the conductive polymers do not possess the blend of (1) toughness, (2) stiffness, (3) elasticity, (4) processibility, (5) impact resistance (and other matrix stress transfer capabilities), (6) retention of properties over a broad range of temperatures, and (7) high temperature resistance that is desirable on aerospace advanced composites. The Prior art composites are often too brittle.

Thermally stable multidimensional oligomers having semiconductive or conductive properties when doped with suitable dopants are also known and are described in our copending applications (including U.S. Ser. No. 773,381 to Lubowitz, Sheppard and Torre). The linear arms of the oligomers contain conductive linkages, such as Schiff base (—N=CH—) linkages, between aromatic groups. Sulfone and ether linkages are interspersed in the arms. Each arm is terminated with a mono- or difunctional end cap to allow controlled crosslinking upon heat-induced or chemically-induced curing.

SUMMARY OF THE INVENTION

Crosslinking imidophenylamines of the general formula:

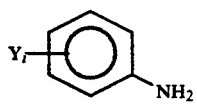

wherein Y =

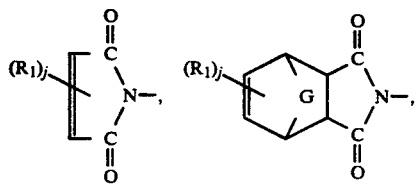

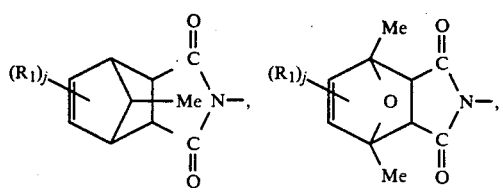

-continued

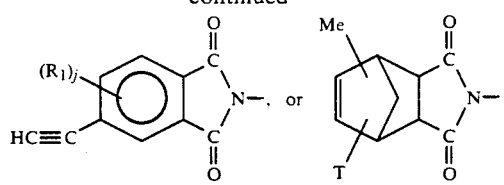

wherein $R_1$ = lower alkyl, lower alkoxy, aryl, aryloxy, substituted aryl, substituted alkyl, halogen, or mixtures thereof;

i = 1 or 2;

Me = methyl;

T = allyl or methallyl;

j = 0, 1, or 2; and

G = —CH$_2$—, —O—, —S—, or —SO$_2$—, are novel compositions of matter.

Preferably,

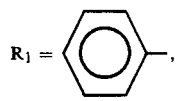

J = 1, i = 2 and G = —CH$_2$—. The highest thermal stability for an oligomer or composite that contains the end cap can be attained if the cap is:

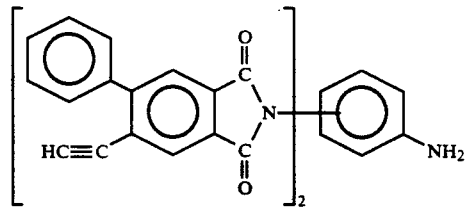

This family can be prepared from the corresponding imidophenyl acid halide of the formula:

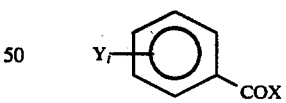

by reacting the acid halide with ammonia to form an acid amide followed by rearrangement of the acid amide to the amine.

The imidophenyl acid halide can be prepared, in accordance with the process described in U.S. Pat. No. 4,604,437, by reacting the corresponding anhydride of the formula:

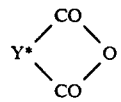

with a corresponding amine of the formula:

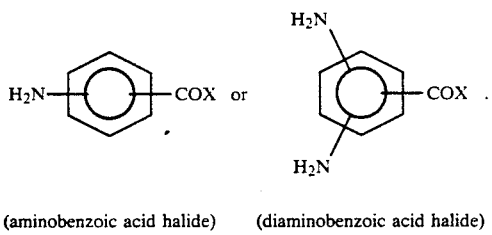

(aminobenzoic acid halide)   (diaminobenzoic acid halide)

This family of imidophenylamines can be used in condensation reactions to form crosslinking, linear or multidimensional oligomers, particularly polyamides or polyimides. For example, the imidophenylamines can be condensed with diacide halides and diamines to form (among others) polyamides of the general formula:

E—NHCO—P—CONH{Q—NH-CO—P—CONH}$_m$ E;

Ar{CONH—P—NHCO—Q—CONH—E}$_n$;

Ar{CONH—E}$_n$; or

Ar{NHCO—Q—CONH—E]

BEST MODE CONTEMPLATED FOR CARRYING OUT THE INVENTION

Crosslinking imidophenylamines useful in advanced composites have the general formula:

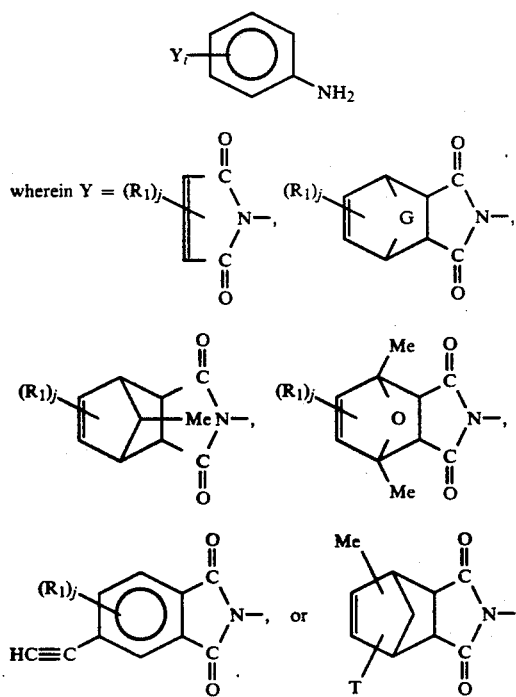

wherein
$R_1$ = lower alkyl, lower alkoxy, aryl, aryloxy, substituted aryl, substituted alkyl, halogen, or mixtures thereof;
Me = methyl;
T = allyl or methallyl;
i = 1 or 2;
j = 0, 1, or 2; and G = —CH$_2$—, —O—, —S—, or —SO$_2$—.

The unsaturation of this family of amines can by thermally or chemically activated after condensing the amine into an oligomer to form crosslinking stability on the cured composite, significantly increasing the solvent resistance of the composites. Imidophenol analogs of these amines are described and claimed in our copending U.S. patent applications 522,676 and 816,489.

These imidophenylamines can be Prepared by reacting the corresponding imidophenyl acid halide of the general formula:

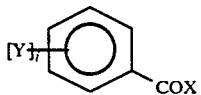

with ammonia to form an acid amide. Rearrangement of the acid amide yields the desired amine.

The acid halide can be prepared from the corresponding acid on the presence of SOCl$_2$. As described in U.S. Pat. No. 4,604,437, the acid is readily prepared by reacting the corresponding anhydride with either aminobenzoic acid or diaminobenzoic acid. Those skilled in the art will be able to prepare the necessary anhydrides by conventional syntheses.

Difunctional imidophenylamines are Preferred, and, in this case, i = 2. Preferably j = 1, G = —CH$_2$—,

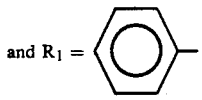

The substituents on the alkyl or aryl radical are generally halo- or hydroxyl- radicals. In accordance with the preferred embodiments, then, the imidophenylamines are:

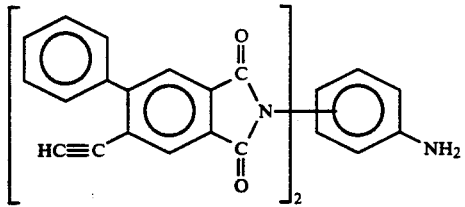

or

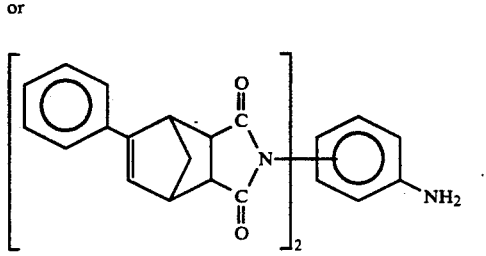

The monomers present a wide range of activation temperatures and, accordingly, provide the desirable end caps for a wide range of curable oligomers. If the end cap is activated near the flow temperature of the polymeric backbone, the best results are obtained.

While preferred embodiments have been described, those skilled in the art will readily recognize alterations, variations, and modifications which might be made without departing from the inventive concept. Therefore, the claims should be interpreted liberally with the support of the full range of equivalents known to those of ordinary skill based upon this description. Accordingly, the claims should only be limited as is necessary in view of the pertinent prior art.

We claim:

1. A method for preparing a crosslinking oligomer comprising reacting an imidophenylamine end cap monomer and a monomer having a functionality reactive with an amine group, the imidophenylamine end cap monomer corresponding to the formula:

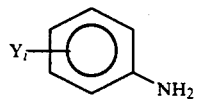

wherein Y =
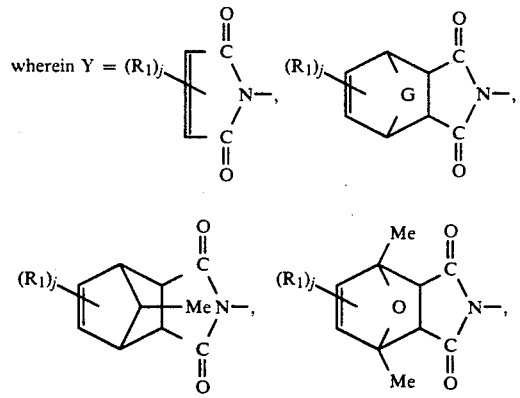

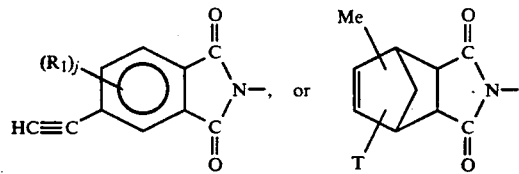

R₁ = lower alkyl, lower alkoxy, aryl, aryloxy, substituted alkyl, substituted aryl, halogen, or mixtures thereof, wherein the substituents for alkyl or aryl are selected from the group consisting of hydroxyl or halogeno;
Me = methyl;
T = allyl or methallyl;
i = 1 or 2;
j = 0, 1, or 2; and
G = —CH₂, —O—, —S—, or —SO₂—.

2. The method of claim 1 wherein Y =

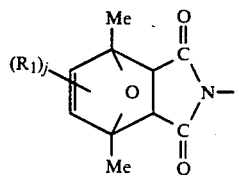

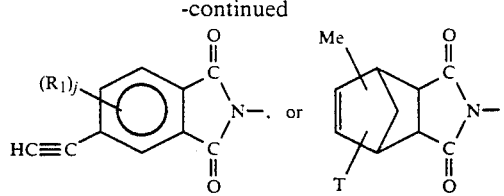

R₁ = lower alkyl, lower alkoxy, aryl, aryloxy, substituted alkyl, substituted aryl, halogen, or mixtures thereof, wherein the substituents for alkyl or aryl are selected from the group consisting of hydroxyl or halogeno;
Me = methyl;
T = allyl or methallyl;
i = 1 or 2;
j = 0, 1, or 2; and
G = —CH₂—, —O—, —S—, or —SO₂.

3. The method of claim 1 wherein i = 1 or 2, and Y =

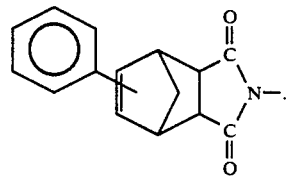

4. The method of claim 1 wherein i = 1 or 2; G = —CH₂—, —CH(CH₃)—, —S—, —O—, or —SO₂—; and Y =

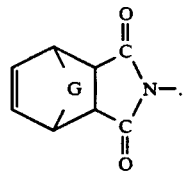

5. A method for preparing a crosslinking oligomer comprising reacting two moles of an imidophenylamine end cap monomer with one mole of an oligomer having two functionalities reactive with an amine group, the imidophenylamine end cap monomer corresponding to the formula:

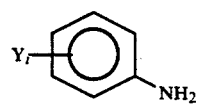

wherein Y =
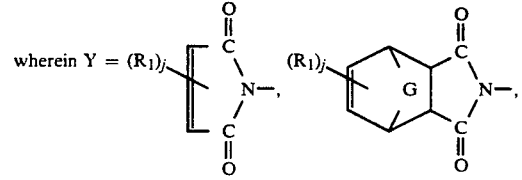

-continued

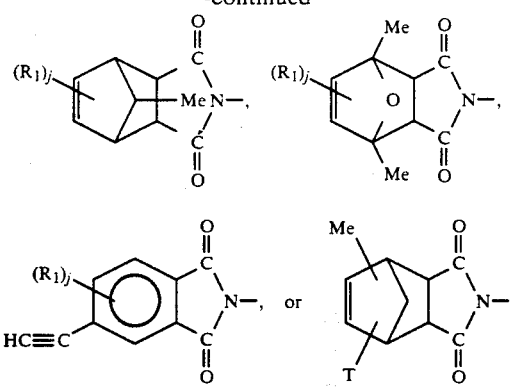

6. The method of claim 5 wherein Y=

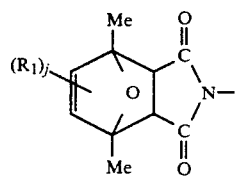

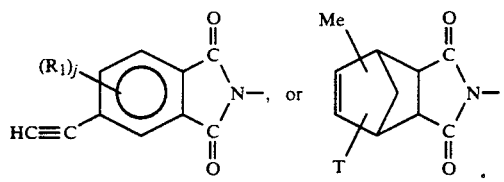

$R_1$ = lower alkyl, lower alkoxy, aryl, aryloxy, substituted alkyl, substituted aryl, halogen, or mixtures thereof, wherein the substituents for alkyl or aryl are selected from the group consisting of hydroxyl or halogeno;
Me = methyl;
T = allyl or methallyl;
i = 1 or 2;
j = 0, 1, or 2; and
G = —$CH_2$—, —O—, —S—, or —$SO_2$.

7. The method of claim 5 wherein i=1 or 2, and Y=

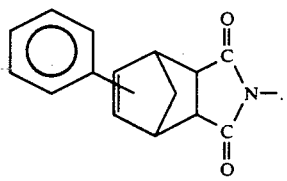

8. The method of claim 5 wherein i=1 or 2; G=—$CH_2$—, —$CH(CH_3)$—, —S—, —O—, or —$SO_2$—; and Y=

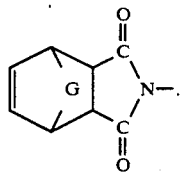

* * * * *